United States Patent [19]

Nochumson et al.

[11] Patent Number: 5,552,325
[45] Date of Patent: Sep. 3, 1996

[54] METHOD FOR SEPARATION AND RECOVERY OF BIOLOGICAL MATERIALS

[75] Inventors: Samuel Nochumson, Randolph; Bruce S. Goldberg, Clifton, both of N.J.

[73] Assignee: FMC Corporation, Philadelphia, Pa.

[21] Appl. No.: 916,801

[22] Filed: Jul. 17, 1992

Related U.S. Application Data

[63] Continuation of Ser. No. 433,259, Nov. 8, 1989, abandoned.
[51] Int. Cl.$^6$ .................................................. G01N 1/18
[52] U.S. Cl. ..................... 436/177; 436/178; 422/70; 422/72; 422/101; 435/272; 210/657; 210/660
[58] Field of Search ............................... 436/177, 178 X; 422/59, 70, 72, 101, 261; 435/288, 270, 272; 210/657, 660

[56] References Cited

U.S. PATENT DOCUMENTS

| | | | |
|---|---|---|---|
| 3,862,030 | 6/1975 | Goldberg | 210/767 |
| 4,066,512 | 1/1978 | Lai et al. | 435/10 |
| 4,142,858 | 3/1979 | Acuff | 422/70 |
| 4,244,694 | 1/1981 | Farina et al. | 422/72 |
| 4,254,082 | 3/1981 | Schick et al. | 422/59 |
| 4,270,921 | 6/1981 | Graas | 422/70 |
| 4,301,118 | 11/1981 | Eddleman et al. | 422/101 |
| 4,373,519 | 1/1983 | Errede et al. | 602/43 |
| 4,422,941 | 12/1983 | Vaughan, Jr. et al. | 210/657 |
| 4,436,820 | 3/1984 | Reiter | 436/178 |
| 4,483,825 | 11/1984 | Fatches | 422/100 |
| 4,496,654 | 1/1985 | Katz et al. | 435/7 |
| 4,508,833 | 4/1985 | Sonneborn et al. | 210/660 |
| 4,523,995 | 6/1985 | Pall et al. | 210/504 |
| 4,557,902 | 12/1985 | Mussmann | 422/59 |
| 4,600,507 | 7/1986 | Shimizu et al. | 210/94 |
| 4,632,761 | 12/1986 | Bowers et al. | 210/650 |
| 4,702,840 | 10/1987 | Degen et al. | 210/638 |
| 4,769,145 | 9/1988 | Nakajima | 210/321.75 |
| 4,787,971 | 11/1988 | Donald | 422/70 |
| 4,800,190 | 1/1989 | Smolik | 502/416 |
| 4,810,381 | 3/1989 | Hagen et al. | 210/657 |
| 4,820,644 | 4/1989 | Schäfer et al. | 422/101 |
| 4,832,851 | 5/1989 | Bowers et al. | 210/650 |
| 4,832,916 | 5/1989 | Gilak | 422/70 |

FOREIGN PATENT DOCUMENTS

| 52-21393 | 6/1977 | Japan | 422/59 |
|---|---|---|---|

OTHER PUBLICATIONS

Berger et al., Methods in Enzymology vol. 152 p. 17 (1987), Academic Press.
Mattiason et al. In Membrane Separations in Biotechnology, McGregor (eds), Marcel Dekker Inc. pp. 99–114 (1986).
Baum et al. In Immobilized Enzymes, Antigens, Antibodies, and Peptides, Weetall (ed), Marcel Dekker Inc. pp. 419–496 (1975).

(List continued on next page.)

Primary Examiner—Donald E. Czaja
Assistant Examiner—Lien Tran
Attorney, Agent, or Firm—Richard E. Elden; Mark A. Greenfield; Polly E. Ramstad

[57] ABSTRACT

Disclosed is a centrifuge tube containing a porous selection means for selectively separating and recovering biological substances from gels, broths, or solutions containing the same, and thus concentrating them, the tube comprising separate upper and lower containers and means for joining the two containers to form a unitary device, the bottom of the upper container comprising a porous selection means, preferably a membrane containing a particulate substance which will selectively bind the biological substances while allowing unbound substances to pass through from the upper to lower container while being centrifuged. A method for recovering the biological substances in high concentration using the centrifuge tube is also provided, comprising introducing said gels, broths, or solutions containing the desired biological substances, centrifuging the same until the desired substance is bound to the selection means, and eluting the bound material from the selection means to recover the substance in concentrated form.

8 Claims, 1 Drawing Sheet

OTHER PUBLICATIONS

Proc. Natl. Aca Sci. USA, 76, No. 2, pp. 615–619 (1979).
Bio Radiations, No. 73, Summer 1989.
"Molecular Cloning: A Laboratory Manual", Maniatis et al. pp. 164–172 & 466–467 (1982).
Bio Rad Bulletin 1402 (1987).
Millipore News, No. 12 (1989).
Kontes Catalog, p. 219 (Nov., 1983).
Electrophoresis, 10 (8–9), pp. 568 and 574 (1989).
"Sequences", Schleicher et al., No. 30, Spring 1989.
Methods in Enzymology, vol. 65, pp. 371–380, Academic Press (1980).
Protein Recovery from Effluents of Microporous Membranes, Bio Pharm, pp. 20–27 (Nov./Dec., 1988).
Millipore Technical Brief TB002 (1989).
Membrane & Separation Technology News, p. 7, Oct., 1980.

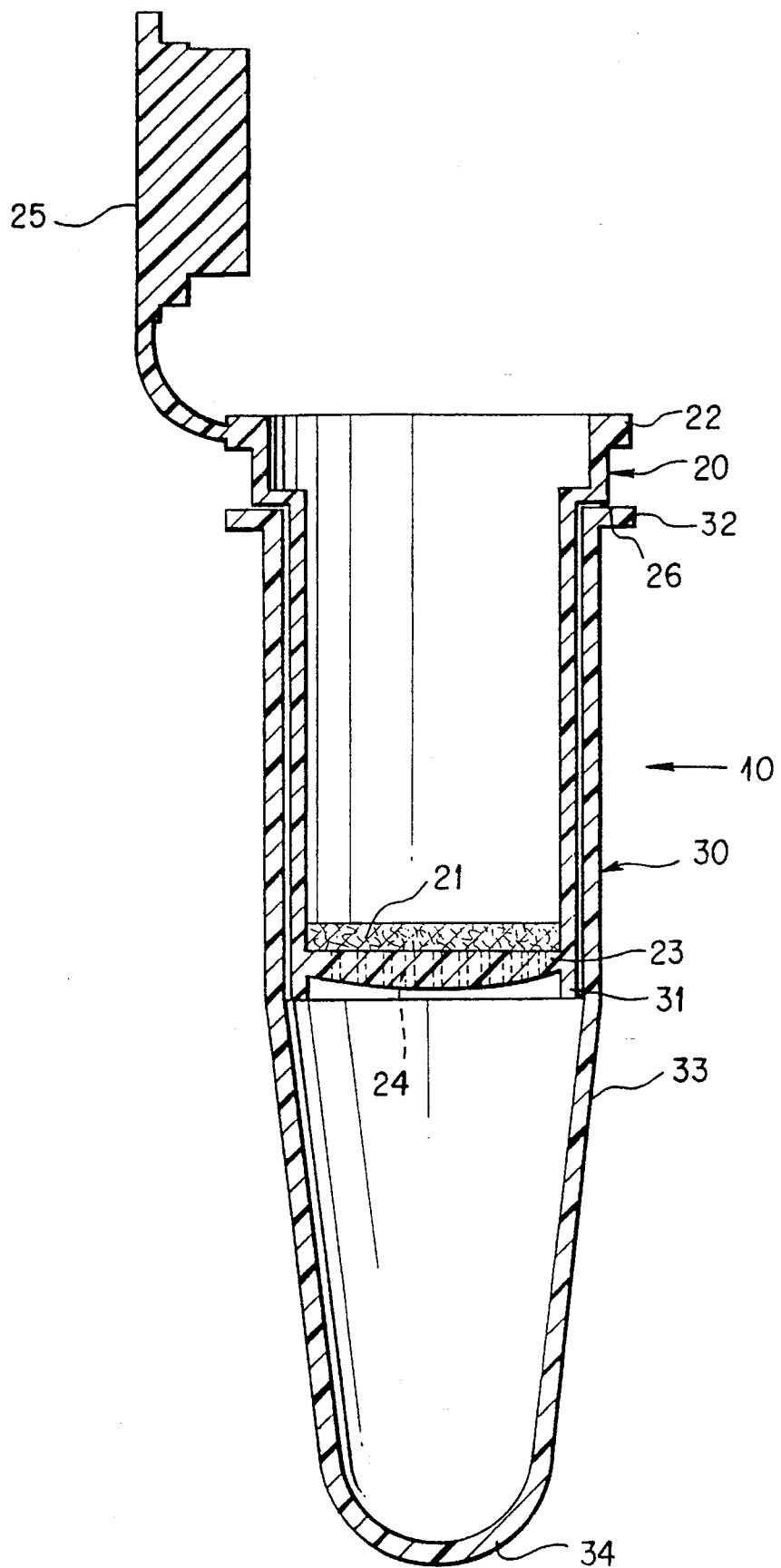

METHOD FOR SEPARATION AND RECOVERY OF BIOLOGICAL MATERIALS

This application is a continuation of application Ser. No. 433,259, filed Nov. 8, 1989 now abandoned.

BACKGROUND OF THE INVENTION

1. Field of the Invention

The present invention is directed to a method for the separation and recovery of certain desired biological substances from liquids containing the same, and to devices for achieving such separation and recovery. More particularly, this invention is directed to the recovery in high concentration of such biological substances as desoxyribonucleic acid (DNA) from liquids containing the same, including broths, gels, or the like, employing an inventive centrifuge tube having affixed therein a porous selection means, as defined herein, to which the liquid is permeable, but which contains sites having an affinity for, and thus selectively binds, the DNA or other biological substance to the selection means. The bound substances may then be recovered from this porous material by elution.

2. Statement of Related Art

Recent advances in molecular biology and like disciplines have required faster and more accurate techniques in the recovery, purification and analysis of small amounts of biological substances such as DNA segments and proteins. Methods such as electrophoresis and other chromatographic separation processes have all required as a necessary step the separation and recovery of these biological materials from gels, broths, or like media, conventionally using either various types of adsorption columns such as ion exchange columns, recovery from gel slices by electroelution or freeze-squeeze techniques; or selective precipitation with e.g., acetone. More recently, an alternate method for recovering DNA from gels after electrophoretic separation has been provided which involves dissolving the desired gel slice in chaotropic salts such as sodium iodide (NaI), followed by selective binding of the DNA to glass beads, i.e. a suspension of silica matrix in water, which is then subjected to centrifugation. *Proc. Natl. Acad. Sci. USA* 76 No. 2, pp. 615–619 (1979). In a similar fashion recent recovery methods include solubilization of the DNA-containing agarose gels, followed by addition of a "purification matrix" to the solution to adsorb the DNA alone. Removal of the adsorbed DNA by a wash buffer, and then centrifugation, recovers the DNA by this elaborate process. Bio-Radiatlons, No 73, Summer 1989 (Bio-Rad Laboratories, Richmond, Va.). See also "Molecular Cloning: A Laboratory Manual", Maniatis et al., pp. 466–467 (Cold Spring Harbor Laboratory, 1982), which also uses a centrifuge tube.

Additionally, various types of test tubes, pipettes, centrifuge tubes, concentrators and like devices in combination with integral filters, and use of these devices in the filtration separation of solids, particularly biological substances, from liquids, liquids from other liquids, and in certain chemical and biological test procedures are already described in the art. See, for example, U.S. Pat. No. 4,557,902 directed to a test tube containing various reagents, for detecting gases, vapors and aerosols, in combination with an internal filter disc separating the reagents. See, also Bio-Rad Bulletin 1402 (1987), (Bio-Rad Laboratories, Richmond, Va.) describing chromatographic spin-column devices and techniques for recovery of radiolabeled nucleotides as well as U S Pat. No. 3,732,981, which discloses columns with removable caps and "snap-off" tips. Acknowledged prior art devices in combination with a filter paper flush with the wall of the tube in a non-filter arrangement are also described, wherein the filter paper is impregnated with a combination of zinc powder, silica gel, inert quartz and silica gel impregnated with gold chloride. Also illustrative of a tube containing a filter medium placed along the axis of the tube rather than in a conventional filtering arrangement is the centrifuge tube of U.S. Pat. No. 4,600,507.

Typical of centrifuge tubes, pipettes and the like having porous membranes arranged across the tube to function as conventional filters are those shown in U.S. Pat. Nos. 4,483,825, to a centrifuge pipette, and 4,301,118 for a protein concentrator. U.S. Pat., Nos. 4,632,761 and 4,787, 971 are cumulative thereto, as well as U.S. Pat. No. 4,832, 851 directed to a highly complex multi-chamber device. See, also, Millipore® News, No. 12 (1989) (Millipore Corp., Bedford, Mass.), as well as corresponding product bulletins, disclosing "low binding membranes" for filtration through centrifuge tubes, which are described favorably as filters with minimum binding, thereby teaching away from membranes which would selectively bind desired biomolecules via centrifugation. Like devices include those shown by the Schleicher and Schuell publication "Sequences", Issue 30, Spring, 1989 (Schleicher and Schuell, Keene, NH, U.S.A.), disclosing their Centrex® filter device, and also the filtration tube of the Kontes catalog of Nov. 1, 1983, at page 219 (item K-413900). (Kontes Co., Vineland, N.J., U.S.A.)

In each device described above the membranes are employed solely as filtration devices, often incorporated in highly complex, intricately engineered devices, none of which teaches the concept of using in combination with a simple centrifuge tube arrangement, a porous selection means containing sites to selectively bind and thereby separate certain biological materials which can thereafter be eluted from the binding site in high concentration.

These methods and devices, while of varying effectiveness, are of limited commercial use in that they are characterized by such complexities as setting up columns; pipetting special reagents, as in the case of glass suspensions; processing only a few samples at a time, as for example, with gel slices; or various associated elution techniques which use toxic solvents, and/or provide low recovery of desired product. See, for example, "Molecular Cloning" (above), pp. 164–172, at p. 164, where it is noted that many methods have been developed to recover DNA from agarose gels, but that none is entirely satisfactory. With the growth of molecular biological research generally, and proposed genome projects in particular, increased facility in selectively separating and recovering a multiplicity of samples of DNA or other biomolecules which avoid such problems would thus be highly desirable.

SUMMARY OF THE INVENTION

In accordance with the present invention there is now provided a novel device, and method of using the same, for selectively separating and recovering in high concentration certain desired biological substances such as DNA or nucleotide segments thereof, radiolabeled DNA or ribonucleic acid (RNA), nick translation products, plasmid DNA, proteins, or the like, or mixtures thereof from liquids containing the same, including broths, gels, or the like wherein the liquid is centrifuged in the inventive device comprising a centrifuge tube of generally cylindrical shape having incorporated therein transverse to the central axis of the tube a porous selection means, generally in the form of one or more polymeric porous sheets or membranes which have integrally incorporated therein sites which selectively bind the biological substance to be recovered while allowing the filtrate to pass through under centrifugal force. The porous selection means may then be washed free of any unbound substance and the bound biological substance recovered from the selection means by various elution techniques.

By the term "selection means" is meant means for selecting certain desired biological substances to be recovered, separated, or resolved from a chromatographic gel or other medium, or from a mixture of biological substances As used herein, such means comprise a matrix or carrier comprising a web, membrane, or other physical configuration of a plastic polymer which is porous, i.e. permeable to liquids and certain undesired materials, but which affords sites capable of selectively (and desirably releasably) binding the desired biological material, such sites being located at moieties integral with the plastic polymer per se or, most preferably, located on or in organic or inorganic particulate entities physically or chemically incorporated within the plastic polymer. Amongst the organic particulates are included both hydrophilic and hydrophobic entities. In the case of composites containing particles incorporated in a plastic polymer, for example, these sites may comprise the surface of the particulate substances per se, e.g. cellulose such as microcrystalline cellulose or more preferably, silica, which binds DNA, and thus provides a DNA selection means.

In a further embodiment, the sites may be the result of chemical activation or modification of the particulate entities such as of silica to which are bound glutaraldehyde or the like as described below, which activated sites provide, for example, a protein selection means. Alternatively, but less preferably, the chemical activation or modification to provide binding sites may be in the form of additions to the porous membrane itself, such as the attachment thereto of biological molecules such as proteins or DNA which themselves may act to bind other biological material. Typical of such protein binding sites are antibodies, antibody binding proteins, lectins, enzymes, or the like.

Other selection means will readily be recognized by those skilled in the art for selectively binding various other biomolecules, and include matrices having incorporated therein other types of cellular, subcellular, biomolecular, organic or inorganic entities capable of binding desired biological materials, including, but not necessarily limited to particulate matter.

By the term "filtrate", as used herein, is meant the liquid filtrate containing any unbound substances, i.e. substances which because of their size were able to pass through the pores of the selection means but because of their nature did not bind to any of the selecting sites, and thus were collected in the bottom of the centrifuge tube. By contrast, the term "ex-filtrate" as used herein refers to unbound substances which because of their size could not pass through the pores of the selection means and thus remained on the surface for later removal.

In thus providing such a ready-to-use cartridge-like device adapted for use in a centrifuge, and containing selection means, particularly ones having a large surface area, there is obtained a flexible method for the rapid recovery of a variety of substances. Advantageously, this device can be scaled down greatly for highly effective use in microfuges to recover minute amounts of biological substances. Moreover, at a relatively low cost compared with prior art techniques, the selection means employed herein, because of their high retention capacity, provide a method for recovering greater than 95% of the desired substance.

The temperature employed is not critical and may be varied widely, but advantageously may be carried out at ambient temperatures in a majority of the cases.

While the selection means may be of any desired thickness consistent with the objectives of the defined process, in a preferred embodiment this material is in the form of a relatively thin membrane. In this form, the membrane should either be sufficiently rigid to withstand centrifugal forces applied to it, or should be incorporated on a porous support within the inventive device. For purposes of this description the porous selection means will be exemplified and referred to hereinafter in its preferred form, i.e. as a porous membrane, and most preferably as a microporous membrane, but it will be understood that any selection means which is porous to fluids or unbound materials, but which selectively binds, by physical or chemical means, specified biomolecules, is intended to be encompassed herein.

In addition to membranes, in a further embodiment there is contemplated thicker, solid state porous selection means having charged groups on or in them which will also selectively bind desired biomolecules to them while allowing liquids to pass through. Typical of these more rigid materials are such substances as cellulosic sheets, as for example ion exchange-activated organic sheets such as diethylaminoethyl (DEAE) cellulose, and the like.

Other examples of suitable porous materials include cast polymeric microporous membranes formed from such materials as nylon, cellulose derivatives, or modified polyvinylidene fluoride; microporous materials formed from fibrils bound together by resins; or like microporous materials known to those skilled in the art. Examples of such materials include those described in U.S. Pat. Nos. 4,702,840; 4,523,995; and 4,800,190.

It is, of course, essential to this invention that the membrane or like selection means has the capability of selectively binding certain desired biological substances which pass through it. The choice of which of the above-described matrices and selection means is appropriate for recovery of any given biological substance is one which can readily be determined routinely by those skilled in the art, depending upon the nature and properties of the substance and the like.

In carrying out this invention there is thus provided a three-phase fractionation of materials wherein the first-phase larger biological or other substances remain on the membrane top surface as an ex-filtrate, and all of the remaining biological substances enter the selection means where as a second phase the desired biological substance is bound, either by selective binding or chromatography, and as a third phase, most of the remaining biological substance passes out of the porous membrane as a liltrate. It is the separation of the second phase bound biological substances that is of primary interest in this invention, and therefore the selection means utilized must be one which has the capability of binding or otherwise retaining only the desired substance, while permitting all of the remaining biological substances to pass through.

Thus, the inventive device must be distinguished from a device utilizing a simple pass-through filter, which achieves only a two-phase separation where the desired material remains in either the filtrate or in the ex-filtrate. While the filtrate or ex-filtrate of this invention may be of further utility, the primary and critical purpose of the invention is to remove the bound or otherwise entrapped biological material in the membrane. The filtration aspect of the membrane thus acts to separate the larger biological material and/or contaminants, such as leukocytes, erythrocytes, and the like on the top, while passing through the biological substances not bound to the membrane.

Several utilities result from this invention's combination of selective binding and filtration. A particularly useful embodiment is the recovery of DNA and/or DNA fragments after they have initially been separated by gel electrophoresis, gel isoelectric focusing, or other gel chromatographic methods, several of which are described in "Molecular Cloning", pp. 164–172 (above). In this embodiment, that portion of the gel which contains the DNA band, (usually agarose or polyacrylamide, but not limited to these substances), is removed, liquefied by any known means, and placed in the top portion of the centrifuge tube. During centrifugation, the gel and any biological material it contains enter the membrane, leaving larger particles, if any, on the surface as an ex-filtrate. DNA present in the gel binds to suitable selection sites in the membrane, such as silica, or microcrystalline cellulose, and the remaining liquefied gel and unbound molecules pass through the membrane as a liltrate. While this method is applicable to DNA segments generally, it is particularly effective for recovery of those segments ranging in size from about 560 base pairs (bp) to 23 kilo base pairs (kb).

The membrane or like means with the bound biological substance is then removed and washed to remove any remaining liquefied gel or other non-bound materials. The DNA or DNA fragments remaining in the membrane are then eluted in a known manner. To facilitate this embodiment, the membrane preferably is removable from the centrifuge tube, although it would be possible for the closed, i.e. bottom, end of the tube to be opened to remove the filtrate and afford a flow-through passage to facilitate washing of the membrane in a similar manner to that disclosed in U.S. Pat No. 3,732,981, which is incorporated herein by reference. In a particularly preferred embodiment, the centrifuge tube comprises a two-section tube comprising a separable upper container in which the selection means is mounted, (although it also is possible for this element itself to be removable from an otherwise integral tube) and a lower container for collecting the filtrate.

Another embodiment of this invention comprises an assay based upon the same three-phase fractional separation and one which, in particular, preferably employs certain chemically activated or modified particulate entities such as silica or cellulose particles, preferably microcrystalline cellulose. In one particular embodiment, for example, a substance to be assayed for the presence of various proteins such as particular antigens or antibodies in whole blood, or, preferably, blood serum, is centrifuged using the inventive device provided with, for instance, an activated silica-containing membrane in which the corresponding antibodies are bound as ligands through such silica-bound chemical groups as polyethylenimine, glutaraldehyde, protein A or protein G or the like, bound to silica; or cellulose such as microcrystalline cellulose, or the like; all of which are integral with the membrane matrix. Thus, for example, there may be bound to the silica in the porous or microporous matrix such chemical groups as glutaraldehyde to bind proteins for enzymatic reactor studies, or for binding anti-bodies, antigens, or selected substrates; carboxymethyl-activated negatively charged silica to separate proteins, bind albumin or IgG; or amino-activated positively charged silica for weak anionic exchange. Alternatively, there may be bound such ligands as the lectin concanavalin A, or Lens culinaris agglutinin. In the case of concanavalin A, this may be employed in affinity-electrophoresis to bind to biantennary glycans. Electrophoresis 1989, 10 (8–9), pp. 568 and 574. Additionally, there may be employed such microporous plastic-silica sheets wherein the silica is activated with sulphopropyl groups to provide a negatively-charged strong cationic exchange binding to separate proteins or the like. Protein G, or protein A may likewise be used as activators in the separation of IgG from albumins or other fermentor supernatants. The described activated silica-microporous sheets are commercially known and available, as for example MPS® sheeting, and are incorporated in ACTI-MOD™ and Acti-Disk™ separation and purification cartridges, all of which are products of FMC Corporation, Philadelphia, Pa., U.S.A. It will be understood, of course, that in addition to use in assays, each of these aforedescribed activated selection means may be employed in the other separation and recovery methods of this invention as well, as described above.

In this "assay" embodiment the critical binding aspect of the selection means "concentrates" the substance to be assayed, by selectively removing it from the filtrate as it perfuses, permitting a sufficient quantity to be bound within the selection means to activate a detector substance which may be any of those known in the art. Where the detector substance creates a color change, the presence of the assayed substance may be indicated by a change in apparent color, or may be indicated using any known biological assay indicator including linked enzymes, radioactive isotopes, spin resonance indicators, nuclear magnetic indicators, fluorescent labels, or the like. Depending upon the nature of the indicator and the degree of concentration achieved by the binding, it may or may not be necessary to wash e.g., the membrane to achieve a positive assay. Where it is necessary or desired to wash the membrane, or to remove the bound substance for completion of the assay, it is preferred to use a removable membrane.

BRIEF DESCRIPTION OF THE DRAWINGS

The drawing is a cross-section of one embodiment of this invention showing a two-section centrifuge tube denoted globally as 10, which incorporates as a selection means a porous membrane.

DETAILED DESCRIPTION OF THE INVENTION

Other than in the operating examples, or where otherwise indicated, all numbers expressing quantities of ingredients, parameters, or reaction conditions used herein are to be understood as modified in all instances by the term "about".

The device of this invention is a tubular container adapted for use in a centrifuge, preferably comprising two sections, the upper portion of which is fitted to or into the lower portion to form a unitary, fluid-tight centrifuge tube. More specifically, the upper portion of this novel device forms a container to receive the fluid samples containing the biological material to be recovered. As an essential feature of this invention, the bottom of this upper portion comprises the aforedescribed porous selection means, and most preferably a porous or microporous membrane or a plurality of membranes, which may be removable, having integrally combined therein certain sites that can selectively bind the biological material to be recovered; which membrane, however, permits the passage of unwanted permeable filtrate which is collected in the bottom portion of the two fitted, sealed sections. Preferably, and especially in the case of sterile substances, the top of the upper container is sealed by known means to prevent contamination. The bottom portion of the device, in which the permeable liquid is collected, is, as described above, fitted with any known sealing means to form a detachable, liquid-impermeable joint with the upper container. This joint may be at a point just below the membrane-formed bottom of the upper container. More preferably, however, as depicted in the drawing, the upper container as a narrower diameter than the lower container such that the upper container will recess into the lower one and be attached thereto by any above-described liquid-impermeable joining means or the like. The upper portion should be removably but sealingly engaged with the lower portion using any means known in the art, such as a gasket or O-ring, dovetail, tapered joint, click-fit, bayonet fit, threaded nipple or the like, or by welding means such as sonic welding, or may be formed integrally with the upper portion, but provided with a circumferential break point below the porous selection means, such as an annular groove.

When so joined, the entire device forms a tube of the type conventionally employed in separating materials in a centrifuge, but which is divided transversely across the axis of the tube by one or more aforementioned porous selection means such as membranes or the like. The exact size and shape of the centrifuge tube is not a critical feature of this invention. However, because very small amounts of biological materials are generally being handled, tubes of a "micro-preparative" scale, for use in microfuges, may be utilized to great advantage.

Shown in the Drawing is a two-section centrifuge tube according to the invention (globally identified as element 10) comprising an upper section (elements 20 through 25) and a lower section (elements 30 through 34).

The upper section comprises: an upper container 20 which is generally cylindrical; a cap 25 which preferably is removably attached to the top of upper container 20, most preferably integral therewith; an annular lip 22 at the top of upper container 20; a flange 26 adapted to bias against the lower section; a bottom 23 comprising a support member preferably integral with lower container 20 having holes or slits 24 adapted to permit the passage of fluid; and a porous selection means, such as a membrane, 21, which entirely covers the bottom 23 so that fluid cannot pass from the interior of the upper container 20 through the holes or slits 24 without first passing through the selection means 21.

The lower section comprises: a lower container 30 adapted to receive upper container 20 and an upper flange 32 adapted to engage flange 26 of upper container 20. Lower container 30 comprises an inward taper 33 toward its rounded bottom 34. The inward taper 33 begins at a circumference 31 located so that the bottom 23 of the upper container 20 biases against it, to afford a friction fit. Upper container 20 is primarily supported by the biasing of flanges 26, 32 against each other, and secondarily supported by the friction fit at circumference 31.

The friction fit at circumference 31, which may be further secured by welding means such as sonic welding, also acts as a substantially fluid impermeable seal, which is useful for handling the centrifuge tube 10 after it has undergone centrifugation. Because the selection means 21 is preferably microporous, fluid placed in upper container 20 generally will not pass through it before being subjected to the forces produced by the centrifugation, and the upper container 20 when its cap 25 is closed can be handled without the need for a stronger fit between the upper and lower sections. When desired, the fit between the upper and lower sections can be by any other known fitting means including threaded nipples, click-fit joints, or the like.

The entire tube 10 may be supported within the centrifuge during its operation by the biasing of the bottom of flange 32 against the centrifuge receiving hole, or may be secured within the centrifuge by any other known means including spacers and/or a complementary-shaped holder.

In an alternative embodiment, not shown, upper container 20 and lower container 30 may be of equal diameter, in which instance they should be securely but removably fastened one to the other along the same central axis.

In operation, as described in further detail below, a gel, broth or solution containing DNA or other biological material to be separated and recovered or assayed, together with substances required to liquefy such fluid (if any), is charged to the upper container 20, which is then or previously fitted into the lower container 30. The entire centrifuge tube 10 is then subjected to centrifugation in a known manner, which causes all matter capable of passing through the pores of selection means 21 to so migrate. The desired biological substance to be separated or assayed becomes bound to the binding sites within the selection means 21, while the remaining filtrate, other biological substances and molecules (if any) are collected at the bottom 34 of the lower container 30. Following centrifugation, the upper container 20 containing the selection means 21 and bound biological substance is separated from lower container 30, and the bound biological substance is eluted in known manner, as described below. Washing of e.g., the membrane, 21, prior to elution of the bound biological substance will result in the removal of any phase of material which is too gross to pass through means 21.

The material used in forming the device, other than the selection means, while not critical, is necessarily one which will not react with or bind the biological material to be recovered, and may be made of glass or metal, or more desirably plastics such as polyethylene, (especially high density), polypropylene, polystyrene, polycarbonate, polytetrafluoroethylene, methyl or polymethyl methacrylate, or like materials as are employed in the manufacture of commercial centrifuge or microcentrifuge tubes (distributed, for example, by Kontes Co., Vineland, N.J., U.S.A.). Because of DNA's ability to bind to glass, it is preferred that the tube not be made of this material when the intended use is with DNA or other like materials which bind to silica.

In a preferred embodiment of the invention, the matrix or web of the selection means to which the biological material is to be bound is a porous, desirably microporous, material, most preferably in the form of a membrane of appropriate thickness, comprised of a polymeric resinous matrix having organic or inorganic entities, preferably in the form particulate binding sites, integrally dispersed throughout, and a network of pores formed within said resinous matrix, as well as between the particles and the resinous matrix, and between neighboring particles, with the size distribution of the pores being relatively non-uniform. Although the invention contemplates selection means wherein the polymer matrix itself may contain integral active binding sites, in this preferred embodiment the resinous matrix should desirably be essentially inert to the biological substances or the liquid mixture in which they are contained, while the pores should be of such a size as to retain the biological substance to be recovered while at the same time allowing the filtrate to pass through to be collected in the detachable lower portion of the device.

The polymers which form the matrix of the membranes employed in this embodiment may vary widely, but are desirably thermoplastic resins made from commercially available polyvinylchloride, or a copolymer thereof with small amounts of monoethylenic monomers such as vinyl acetate, vinylidene chloride, propylene, ethylene, or mixtures thereof. Alternatively, the matrix may be formed from such materials as polytetrafluoroethylene (PTFE), cellulose acetate or triacetate, polyamides, such as nylon, polysulfone, cellulose nitrate; mixtures or alloys thereof; or the like. In general, however, any thermoplastic resin which is readily plasticized by a solvent, or is sinterable by heat or pressure, or which can be readily rendered from a previous matrix, and which is chemically and physically stable under conditions used in this invention may be so employed.

The dispersed particulate matter is preferably silica, or chemically-activated silica, as described above, desirably in the form of commercially available silica hydrogel or precipitated hydrated silica; or a cellulose such as microcrystalline cellulose, but may comprise other selected materials, both organic and inorganic, which act to bind and separate the desired biological substance. Also included amongst the particulate matter which may be employed are inorganic materials such as aluminum hydroxide, aluminum oxide, titanium dioxide, ferrous hydroxide, hydrated absorbent clays or diatomaceous earths, borax, and hydroxyapatite, all of which may be used to bind DNA. Alternatively, organic materials, including both hydrophilic and hydrophobic materials, such as particles of hydroxyethyl cellulose, hydroxymethyl cellulose, dextran, alginic acid, acetyl salicylic acid, polyacrylate/cellulose graft polymers, cross-linked polyacrylates, collagen, agarose, chitosan, hydroxyl-bearing gums such as galactomannans, glucomannans, β-1, 3-curdlans, konjac, and mixtures thereof or the like may be employed.

For purposes of this description, the preferred particulate for binding DNA, namely silica, will be used hereinafter when describing recovery of DNA, particularly from gels such as agarose. See, e.g., Proc. Natl. Acad. Sci. USA, (above).

The amount of particulate matter, relative to the total weight of the selection means, is not critical but is desirably in the range of 10 to 90% w/w, preferably 40 to 60% w/w.

One porous material having suitable particles incorporated therein which may be employed as the membrane in the device and process of this invention, is described in U.S. Pat. No. 3,862,030, issued Jan. 21, 1975 to Bruce S. Goldberg, which patent is incorporated in this description by reference. As described therein, the pores are formed within the resinous matrix between the matrix and the particles, and between the particles themselves.

These membranes may be prepared in various ways known in the art. Thus, in accordance with one preferred embodiment there is disclosed in the above-mentioned U.S. Pat. No. 3,862,030 the method of forming microporous sub-micron membranes comprising the following steps:

a. forming the composition comprising the mixture of a polymeric resin, inorganic or organic particles, the particles being present in an amount by weight ranging from about 1 part per part of polymer, to about 2 parts per part of polymer; a solvent, such as cyclohexanone, which is present in an amount by weight ranging from about 1.5 parts per part of polymer to about 3 parts per part of polymer; and a non-solvent (preferably water), which is present in an amount by weight ranging from about 1 to about 1.3 times the amount of the solvent, which solvent comprises at least 30% of the total composition by weight;

b. extruding or molding said composition at room temperature or above to form a membrane comprising a substantially flattened sheet;

c. passing the flattened sheet through an extraction medium to replace the solvent in the sheet with the extraction medium; and d. removing said extraction medium from said sheet. One such typical membrane prepared by this process is an MPS® membrane (FMC Corporation, Philadelphia, Pa., U.S.A.), which is a microporous polyvinylchloride-silica sheet with a porosity volume in the 70–80% range. The pore size, as determined by mercury intrusion porosimetry, is in the 0.2 μm to 2.0 μm range. The support is extremely hydrophilic, has a negative charge that can be changed to positive, and a surface area of 80 $m^2/g$. This material is non-compressible under normal conditions, steam sterilizable, and has a low dry density of 0.45 $g/cm^3$. The active sites are attributed to the silica contained within the porous matrix which allows the addition of organic functionability via silica attachment chemistries. Moreover, it has been found that this MPS membrane, for example, has a DNA binding capacity of at least about 260 $\mu g/cm^2$.

In addition to the above-described membranes, there may also be employed in this invention certain membranes having a polytetrafluoroethylene (PTFE) fibril matrix such as is described in U.S. Pat. No. 4,373,519 (3-M Corp., Minneapolis, Minn., U.S.A.), which is also incorporated herein by reference.

These membranes, in sheet form, comprise:

a. a polytetrafluoroethylene fibril matrix; and b. 0.5 to 10 parts of hydrophilic absorptive particles per part of PTFE by weight enmeshed in said matrix, the absorptive particles having absorptive capacity greater than 0.5 grams of water per gram of dry particle.

To prepare this membrane the hydrophilic particles are incorporated into a PTFE emulsion to form a paste, which is subjected to a great amount of shear causing the PTFE to fibrillate and enmesh the particles into a fibrillar matrix. There are many processes of fibrillating PTFE and virtually all non-sintering processes are adaptable to the method of making the composite of the instant invention. The most suitable, however, is that described by Ree et al. in U.S. Pat. No. 4,152,661.

Basically, the fibrillation involves the formation of a paste of water swollen particulate material and PTFE particles, intensive mixing at 50° to 20° C., biaxial calendering, and a drying step. This results in a membrane with PTFE fibrils having a thickness in the range of about 0.025 to 0.5 micrometers.

The size of the absorbent-type particles are within a broad range of 0.1 to 300 micrometers when dry. Preferably, the particle size range of the hydrophilic polymer absorbent is 1.0 to 80 micrometers. The particles have an absorptive capacity greater than 0.5 (i.e., in the range of 0.5 and 40 grams) of water per gram of dry particles.

The hydrophilic absorbent for the PTFE membrane may be particles comprised of alginic acid, polyacrylate-cellulose graft copolymer, collagen, chitin, chitosan, clay, casein, zein, dextran, carboxymethyldextran, starch, modified starch, hydroxyethyl starch, hydrolyzed polyacrylonitrile, starch-methacrylonitrile polymer, polyacrylamide, hydrolyzed polyacrylamide (Separan® AP-30 from the Dow Chemical Co., Midland, Mich., U.S.A.), cellulose, carboxymethylcellulose, and derivatives or mixtures of the aforementioned materials. One preferred material is a cross-linked dextran derivative, having a water absorptive capacity between 2 g and 10 g of water per gram of dry material. Satisfactory volume absorption is in the range of 0.1 to 10 mm, preferably in the range of 0.25 mm to 5 mm.

Hydrophilic absorbent particles may be admixed with inert less-absorptive diluent particulates which range in size from 0.1 to 100 micrometers to improve the handling characteristics of the composites and to facilitate their manufacture. Examples of diluent particles include powdered polymers such as polyethylene, polypropylene, and polystyrene, and inorganics such as kaolin, talc, silica, bentonite, and vermiculite.

The particulate material in this PTFE membrane accounts for from 40 to 90%, and preferably 80–90%, by weight of the total composition, of which up to 50% can be inert diluent particles. The most preferred amount of total particulates is about 85% by weight.

Additional porous membranes containing sites which will selectively bind DNA and the like include silica-based matrices made by J. T. Baker Co. (distributed by Sargent-Welch Scientific Company, Skokie, Ill., U.S.A.). Matrices such as borosilicate glass microfilters from E-D Scientific Specialties (Carlisle, Pa. U.S.A.) containing such silica gels may also be successfully employed in the device and method of this invention.

As stated above, this invention contemplates, in one preferred embodiment, the method of recovering DNA from gels by centrifuging the liquefied gels or like materials in a tube containing the aforedescribed porous selection means, preferably a silica-containing membrane, thereby binding the DNA to the membrane while the remaining liltrate passes through the membrane, and recovering the concentrated DNA from the membrane by elution. More particularly, when DNA-containing gels from electrophoretic chromatography methods are thus treated, it is essential that the process be carried out in the presence of one or more chaotropic salts, i.e. salts which disrupt the binding of water to agarose or like media, and thus enhance the binding of the DNA to the binding sites, including such salts as NaI, perchlorates, SCN$^-$ salts and the like, but preferably NaI.

The amount of salt used if not critical may vary widely, depending upon the salt and its solubility, but desirably should be present in high concentrations known to those skilled in the art, generally near saturation, relative to the amount of gel or solution being treated.

Following centrifugation, at which time the DNA is selectively bound to the membrane, the filterable liquid is forced through the membrane into the lower container for discarding, and any non-filterable, insoluble substances are collected on and/or in the membrane surface and pores, the membrane is then washed to remove NaI and/or the non-filterable substances, and the DNA eluted from the membrane with water or a suitable low ionic strength solution such as tris-(hydroxymethyl) aminomethane ("Tris") from which it may then be recovered in concentrated form by, e.g., precipitation.

In carrying out the washing step to remove the NaI or other chaotropic salts prior to elution, it is important that the amount of salt in the washing solution be adjusted so as not to also wash off the bound DNA. This may readily be achieved by using a buffered solution which is low in alcohol concentration and of high enough ionic strength using, for example NaCl. Following this washing step the DNA may then be eluted by a separate buffered solution, desirably one which is low in salt concentration. In any event, in each of these two steps, the exact nature of the buffered solution can be routinely varied as to pH, salt concentration, alcohol concentration, and the like in a known manner by those skilled in the art in order to maximize the recovery of DNA or other bound biomolecule. Thus, for instance, as shown in the examples, small variations in the concentration of the reagents can significantly affect the amount of DNA recovered.

Each of the above binding, washing, eluting, and concentration steps may be carried out using techniques known to those skilled in the art. In one preferred embodiment, the process may be carried out by the following protocol, using the above-described inventive device:

1) Add two volumes (20 µl) of saturated sodium iodide to a DNA sample (for recovery studies typically there are 2 µg of DNA in a volume of 10 µl). If the sample is a solution sample, it may be applied to the unit at once; if the sample is a gel slice, it should first be dissolved, desirably by adding two volumes of saturated NaI solution to the gel slice (if high-melt agarose in Tris-borate-EDTA (TBE) buffer use 3 volumes of 8M NaClO$_4$), where EDTA is ethylenediaminetetraacetic acid. Warming to 55°–60° C. for 5 minutes will accelerate dissolution. (While this works for Tris-acetate buffer systems, gel does not dissolve as well if the Tris-borate buffer system is used.)

2) Introduce sample into inventive device (microcentrifuge tube), and allow it to incubate at room temperature for about 60 seconds.

3) Spin in a microcentrifuge for about 15–30 seconds (collect flow-through in bottom portion of microcentrifuge tube).

4) Wash 3 times with 100 µl aliquots of ice cold wash buffer (10 mM Tris, pH 8.0; 50% ethanol; and 200 mM NaCl, used to help keep the DNA bound to the binding sites) by applying each aliquot to the unit and spinning it through as in step 3. (Other solutions such as 80% ethanol also work reasonably well.) It is important to maintain a high enough ionic strength to avoid washing off bound DNA.

5) Remove the residual ethanol by incubation in a vacuum dessicator, or incubator, at 55° C. For many applications residual ethanol may not be a problem; for applications involving subsequent treatment of the sample with enzymatic systems, total removal of any residual ethanol is important.

6) Apply 20 µl of TE (i.e., 10 mM Tris; 1 mM EDTA, pH 8.0), incubate for one minute then spin in a fresh centrifuge tube. Repeat the process with a second 20 µl aliquot. Initial elution appears to remove about 70–80% of the sample, while recoveries improved to about 90% using a second elution. The volumes stated here are minimal values; larger volumes may be used for applications where a high sample concentration is not important. If necessary, the sample can be concentrated by ethanol precipitation (a standard method) at this point prior to subsequent processing.

The following examples will now illustrate the invention.

EXAMPLE 1

To bacteriophage lambda DNA cut with Hind III restriction endonucleases and end-labeled with $^{32}$PdCTP was added 2 volumes of a saturated (8.0 M) NaI solution, and the resulting solution centrifuged at room temperature for 2 minutes at 13,000 g in a 1.5 ml (SPINBIND™) centrifuge tube according to this invention containing a silica-filled polyvinylchloride MPS® membrane, where the weight ratio of silica to membrane is about 50:50 (SPINBIND and MPS are trademarks of FMC Corporation, Philadelphia, Pa., U.S.A.).

The recovered membrane was then rinsed with a wash buffer of 50% ethanol, 10 mM Tris, 100 mM NaCl, and 1.0 mM of EDTA (pH 7.2). Optionally, prior to this washing the membrane may first be backwashed in a known manner in order to remove any protein, nucleotides, or like insoluble materials from the surface or pores of the membrane.

Recovery of the bound DNA from the membrane was achieved by eluting it with 50 µl of a low salt buffer containing 10 mM Tris-HCl (pH 8), and 1 mM EDTA. Measurement of applied radioactivity showed a 95% recovery of DNA, as shown in the following table.

TABLE I

| Step | CPM[a] | Recovered (%) |
|---|---|---|
| Sample | 288,750 | 100 |
| Unbound | 4,150 | 1.4 |
| Wash (4 × 100) | 13,000 | 4.5 |
| Elution (250 µL) | 274,300 | 95 |

[a]CPM = counts per minute.

In accordance with the foregoing procedure, but substituting $^{35}$S-end labeled DNA (a commercial preparation from Amersham Corp. Arlington Heights, Ill.) for the above $^{32}$-p end-labeled DNA, there was recovered only about 35–40% of the S-labeled material. This decrease in recovery is believed to be due to the presence of the $^{35}$S label itself. This was demonstrated by running a mixture of $^{35}$S- and $^{32}$p- end labeled DNAs, in the same manner as Example 1, in which 90–95% recovery of the $^{32}$P-labeled DNA was obtained.

EXAMPLE 2

The SPINBIND™ centrifuge tube of Example 1 was used to bind and elute the linearized pBR322 DNA. Once the DNA was bound, buffers varying in NaCl concentration and ethanol percentage as shown in the table below were used to wash the NaI (DNA binding buffer) off the centrifuge tube's membrane.

The following protocol for DNA binding and elution was employed: 2 µg of linearized pBR322 DNA was loaded per unit; DNA was eluted in two 25 µl aliquots of 10 mM Tris, (pH 7.5); and the recovered DNA was lyophilized and re-suspended in 50 µl of 10 mM Tris, (pH 7.5). Thereafter, re-suspended DNA was electrophoresed and quantitated by comparison of photographs of the ethidium bromide stained gel with standard photos. Nick translations were performed with known enzymatic labeling procedures using BRL's Nick Translation Kit, (BRL Corp., Gaithersburg, Mo., U.S.A.) using 50 µCi (microcures) of alpha-[$^{32P}$]dCTP (cytidine triphosphate) per reaction, 400 Ci/mmol. The table below lists the recovery of linearized pBR322 DNA from the SPINBIND™ unit after "washing" off the residual NaI with 10 mM Tris containing the indicated NaCl and ethanol concentrations. Also listed is the relative incorporation of $^{32}$p, as percent of control, for nick translated DNA.

TABLE II

| 10 mM Tris mM NaCl | Wash Buffer % EtOH | % DNA Eluted | Rel. Incorp'n $^{32}$P (% of Control)[a] |
|---|---|---|---|
| 200 | 50 | 60 | 18 |
| 100 | 50 | 75 | 54 |
| 50 | 50 | 25 | xx[b] |
| 50 | 70 | 65 | 13 |
| 0 | 70 | 75 | 20 |
| 0 | 80 | 100 | 32 |

[a]Control was nick translated linearized pBR322 DNA, labeled to 8 × 10$^7$ cpm/µg.
[b]Insufficient DNA was recovered to perform the nick translation.

From the above it will be seen that best recoveries were following washes using buffer without NaCl, containing 80% and 70% EtOH, (100% and 75% recovery, respectively); better elution was obtained with 100 mM NaCl (75%) than with 200 mM NaCl (60%), i.e., by using 50% EtOH as wash buffer and halving the NaCl concentration, there was obtained a significant increase in specific activity of labeled DNA: 18% of control with 200 mM NaCl vs 54% of control with 100 mM NaCl.

EXAMPLE 3 (Comparison)

Two commercially available centrifuge tubes whose physical structure was very similar to those employed in Examples 1 and 2, except that they used filtration membranes instead of a selection means as defined herein, were compared with the device of this invention to determine the effectiveness of each in the recovery of DNA from a solution containing the same. In the following example a microporous membrane-containing tube (Millipore ULTRAFREE®-MC with a 0.45 µm Durapore membrane—Millipore Corp., Bedford, Mass.) and an ultrafiltration membrane-containing tube (Millipore ULTRAFREE®-MC with 30,000 NMWL (nominal molecular weight) PTTK polysulfone membrane—Millipore Corp.) were compared with the MPS membrane-containing device (SPINBIND™) of Example 1.

Two volumes (20 µl) of saturated sodium iodide were added to 10 µl samples containing 2 µg of bacteriophage lambda DNA digested with restriction endonuclease BstE II. Samples were applied to each of the three units being tested and after incubating at room temperature for 1 minute the units were spun in a microcentrifuge for 30 seconds. Aliquots (10 µl) of the flow through were held for subsequent analysis by gel electrophoresis. The membranes were washed 2×with 100 µl aliquots of ice cold wash buffer (10 mM Tris pH 8.0, 200 mM NaCl, 50% ethanol). Aliquots (15 µl) of the first wash were saved for later gel analysis. Residual ethanol was removed by incubation at 55° C. Aliquots (40 ) of low salt buffer (10 mM Tris, 1mM EDTA pH 8.0) were then applied to the units. After a one minute incubation the units were centrifuged to elute the DNA (at least from SPINBIND™ unit) from the units. Aliquots (2 µl) were saved for later gel analysis.

The sample aliquots were run overnight on a 1% Sea Kem® LE agarose gel at a voltage gradient of 1V/cm. Analysis of the gel revealed that both the SPINBIND™ unit and the unit with the ultrafilter showed very little material passing in the flow through from loading. The unit with the microporous membrane showed that almost all of DNA passed through in the initial loading spin. The samples from the washing step showed that the only wash which contained a detectable amount of DNA was that from the microporous membrane. The samples from the elution step showed that the DNA which had been bound to the SPINBIND™ unit had indeed been eluted, and that a small amount of DNA leaked around the ultrafiltration membrane. Basically the results were as expected; in the prior art devices the DNA either passed through the membrane at once or was blocked by the membrane. In neither case was the DNA specifically bound, as in the case of the SPINBIND™ unit.

We claim:

1. A method for selectively separating and recovering desired biological substances from liquids containing the same which comprises centrifuging said liquid in a centrifuge tube wherein said tube is divided into a separable upper container and lower container, the bottom of said upper container being comprised of a porous selection means capable of selectively binding desired biological substances thereto while allowing filtrate to pass therethrough, said porous selection means comprising a porous membrane containing an integrally bound particulate affording binding sites distributed throughout said membrane, thereby binding said biological substances to the selection means, and recovering the bound biological substances from the selection means by elution.

2. A method for selectively separating and recovering in concentrated form desired biological substances from liquids containing the same which comprises centrifuging said liquid in a centrifuge tube wherein said tube is divided into a separable upper container and lower container, the bottom of said upper container being comprised of a porous selection means capable of selectively binding desired biological substances thereto while allowing filtrate to pass therethrough, said porous selection means comprising a porous membrane containing an integrally bound particulate affording binding sites distributed throughout said membrane, thereby forming a first phase comprising unbound biological substances on the surface of the selection means or in the pores thereof, a second phase comprising the biological substances bound to the selection means, and a third phase comprising any filtrate in the lower container and recovering the bound biological substances.

3. The method of claim 1 or 2 wherein said liquid comprises a liquefied agarose gel containing deoxyribonucleic acid and the method is carried out in the presence of a chaotropic salt.

4. The method of claim 3 wherein the chaotropic salt is sodium iodide.

5. The method of claim 1 or 2 wherein the selection means binding sites are capable of selectively binding deoxyribonuclec acid, radiolabeled deoxyribonucleic acid or ribonucleic acid, proteins, or nick translation products.

6. The method of claim 5 wherein the binding sites are inorganic particulate entities comprising aluminum hydroxide, aluminum oxide, titanium dioxide, ferrous hydroxide, hydrated absorbent clays or diatomaceous earth, borax, silica or mixtures thereof.

7. The method of claim 5 wherein the binding sites are organic particulate entities comprising microcrystalline cellulose, hydroxyethylcellulose, hydroxymethylcellulose, dextran, alginic acid, acetyl salicylic acid, polyacrylate/cellulose graft copolymer, crosslinked polyacrylates, collagen, agarose, chitosan, hydroxyl-bearing gums, or mixtures thereof.

8. The method of claim 1 or 2 wherein the biological substance is unlabeled or $^{32}$P-labeled DNA, and the selection means is a silica-filled polyvinylchloride membrane.

* * * * *

UNITED STATES PATENT AND TRADEMARK OFFICE
CERTIFICATE OF CORRECTION

PATENT NO. : 5,552,325
DATED : September 3, 1996
INVENTOR(S) : Samuel Nochumson and Bruce S. Goldberg It is certified that error appears in the above-indentified patent and that said Letters Patent is hereby corrected as shown below:

Column 1, line 49, "Bio-Radiatlons" should read --Bio-Radiations--.
Column 4, line 54, "liltrate" should read --filtrate--. Column 5, line 23, "liltrate" should read --filtrate--. Column 11, line 33, "liltrate" should read --filtrate--.

Signed and Sealed this

First Day of April, 1997

Attest:

BRUCE LEHMAN

Attesting Officer

Commissioner of Patents and Trademarks